(12) United States Patent
Varghese et al.

(10) Patent No.: US 11,344,368 B2
(45) Date of Patent: May 31, 2022

(54) LIGHT BASED SKIN TREATMENT DEVICE AND METHOD

(71) Applicant: KONINKLIJKE PHILIPS N.V., Eindhoven (NL)

(72) Inventors: Babu Varghese, Eindhoven (NL); Rieko Verhagen, Vught (NL)

(73) Assignee: Koninklijke Philips N.V., Eindhoven (NL)

( * ) Notice: Subject to any disclaimer, the term of this patent is extended or adjusted under 35 U.S.C. 154(b) by 255 days.

(21) Appl. No.: 16/324,328

(22) PCT Filed: Aug. 8, 2017

(86) PCT No.: PCT/EP2017/070072
§ 371 (c)(1),
(2) Date: Feb. 8, 2019

(87) PCT Pub. No.: WO2018/029194
PCT Pub. Date: Feb. 15, 2018

(65) Prior Publication Data
US 2019/0201098 A1 Jul. 4, 2019

(30) Foreign Application Priority Data

Aug. 9, 2016 (EP) ..................... 16183299
Aug. 9, 2016 (EP) ..................... 16183301
(Continued)

(51) Int. Cl.
*A61B 18/00* (2006.01)
*A61B 18/20* (2006.01)

(52) U.S. Cl.
CPC .... *A61B 18/203* (2013.01); *A61B 2018/0047* (2013.01); *A61B 2018/00107* (2013.01);
(Continued)

(58) Field of Classification Search
None
See application file for complete search history.

(56) References Cited

U.S. PATENT DOCUMENTS 4,733,660 A * 3/1988 Itzkan .................. A61B 18/203
606/9
5,868,731 A 2/1999 Budnik et al.
(Continued)

FOREIGN PATENT DOCUMENTS

EP 0172490 A1 2/1986
EP 3001989 A1 4/2016
(Continued)

OTHER PUBLICATIONS

Habbema, L. et al., "Efficacy of Minimally Invasive Nonthermal Laser-Induced Optical Breakdown Technology for Skin Rejuvenation", Lasers in Medical Science 28 (3), pp. 935-940, Aug. 14, 2012.
(Continued)

*Primary Examiner* — Gary Jackson
*Assistant Examiner* — Anant A Gupta

(57) ABSTRACT

A pulsed laser skin treatment device is for laser induced optical breakdown of hair or skin tissue. A beam scanning system scans the beam to define a circular or arc path, using a rotated prism which implements a lateral shift to the beam. A focusing system at the output side of the beam scanning system focuses the incident light beam into a focal spot in the hair or skin tissue, and it rotates with the prism.

18 Claims, 9 Drawing Sheets

(30) Foreign Application Priority Data

Dec. 28, 2016 (EP) .................................... 16207164
Dec. 30, 2016 (EP) .................................... 16207590

(52) U.S. Cl.
CPC ............ *A61B 2018/00452* (2013.01); *A61B 2018/00476* (2013.01); *A61B 2018/202* (2013.01); *A61B 2018/20355* (2017.05); *A61B 2018/20359* (2017.05); *A61B 2018/20361* (2017.05); *A61B 2018/20553* (2017.05)

(56) References Cited

U.S. PATENT DOCUMENTS

| | | | |
|---|---|---|---|
| 6,325,794 B1* | 12/2001 | Yoon | A61B 18/22 606/17 |
| 8,506,559 B2 | 8/2013 | Raksi | |
| 9,974,691 B2 | 5/2018 | Donitzky et al. | |
| 2008/0287930 A1* | 11/2008 | Rapoport | B23K 26/0096 606/9 |
| 2010/0069897 A1 | 3/2010 | Spikker | |
| 2010/0130968 A1* | 5/2010 | Vogler | A61F 9/008 606/5 |
| 2011/0118713 A1* | 5/2011 | Raksi | A61F 9/00814 606/6 |
| 2012/0123444 A1 | 5/2012 | Varhagen | |
| 2012/0283709 A1* | 11/2012 | Reichert | A61N 5/0616 606/9 |
| 2012/0283711 A1 | 11/2012 | Liu | |
| 2012/0310224 A1 | 12/2012 | Miyagi | |
| 2014/0005643 A1* | 1/2014 | Chang | A61B 18/203 606/9 |
| 2014/0364840 A1 | 12/2014 | Donitzky | |
| 2015/0051593 A1* | 2/2015 | Johnson | A61N 5/0616 606/9 |
| 2015/0133848 A1 | 5/2015 | Bratchenia | |

FOREIGN PATENT DOCUMENTS

| | | |
|---|---|---|
| WO | WO2005011510 A1 | 2/2005 |
| WO | WO2008001284 A2 | 1/2008 |
| WO | WO2013128380 A1 | 9/2013 |
| WO | WO2018029196 A1 | 2/2018 |

OTHER PUBLICATIONS

Habbema, L. et al., "Minimally Invasive Non-Thermal Laser Technology Using Laser-Induced Optical Breakdown for Skin Rejuvenation," Journal of Biophotonics 5 (2), pp. 194-199, Nov. 1, 2011.

* cited by examiner

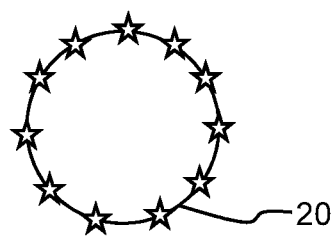
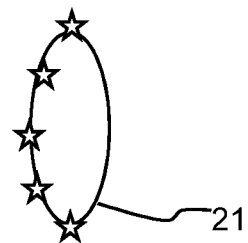
Fig. 2A              Fig. 2B
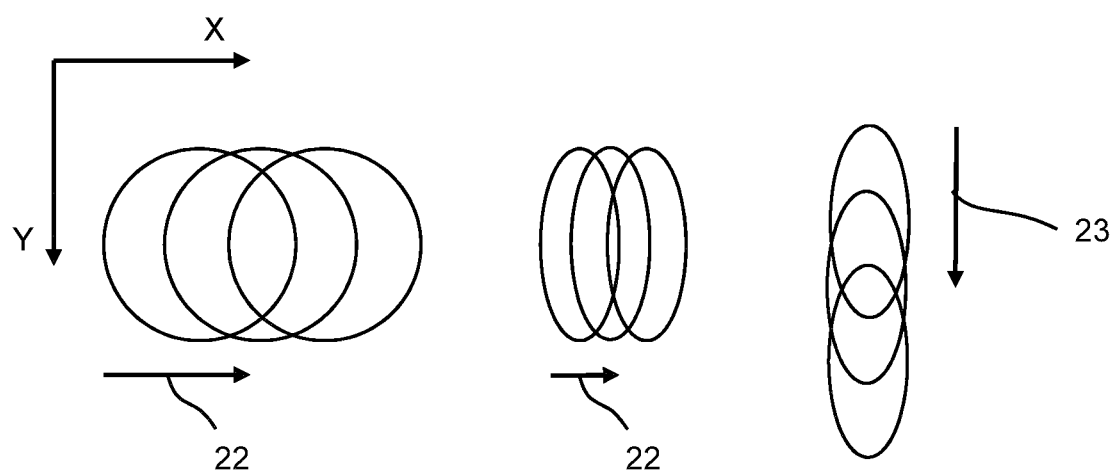
Fig. 2C              Fig. 2D

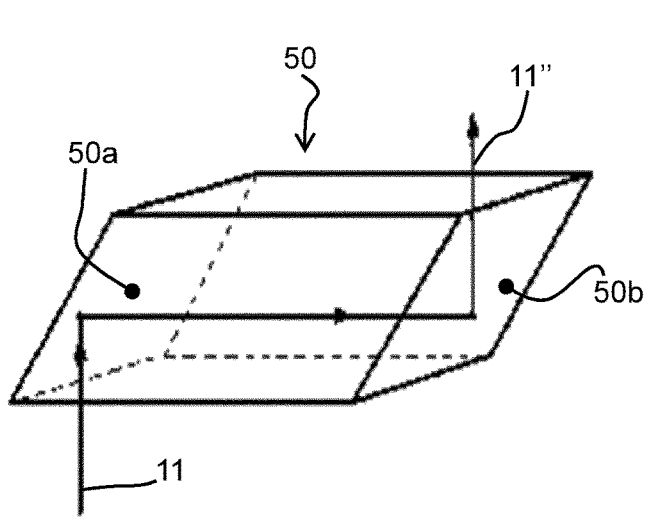
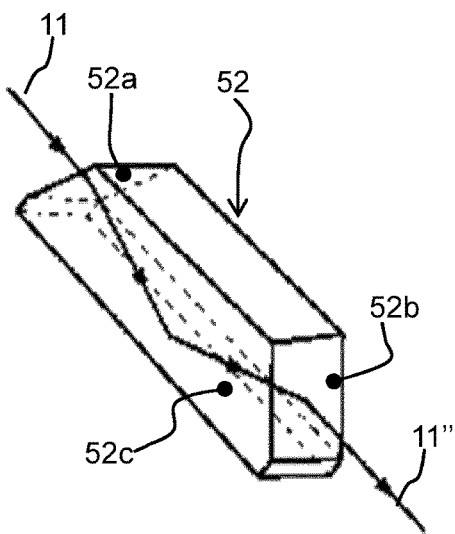
FIG. 5A  FIG. 5B
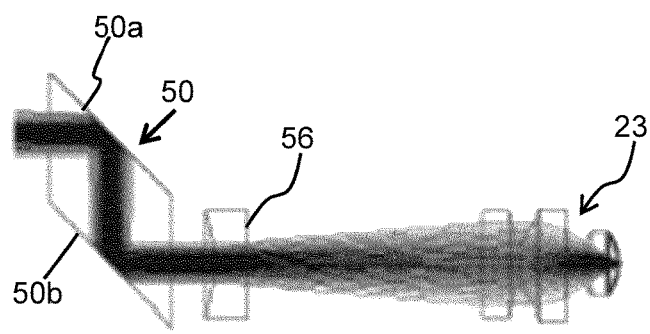
FIG. 5C
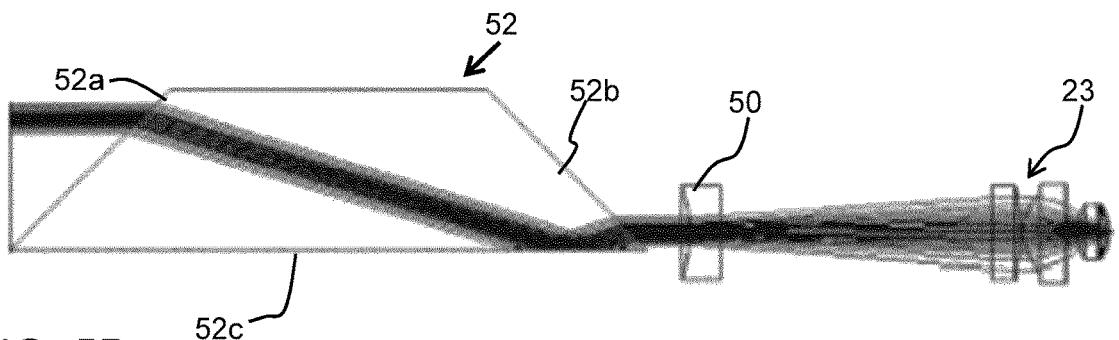
FIG. 5D

LIGHT BASED SKIN TREATMENT DEVICE AND METHOD

FIELD OF THE INVENTION

This invention relates to a device for generating laser induced optical breakdown in mammal tissue such as skin tissue and as such can be used for (cosmetic) treatment of humans or animals. The device may thus be a skin treatment device or an in-body treatment device such as endoscope or catheter. The device comprises a light source and a focusing system for focusing the incident light beam of the light source in a focal spot located outside the device such that the focal spot can be positioned in the tissue below a boundary (surface) of the tissue (e.g. skin, organ boundary) to cause laser induced optical breakdown of the tissue at the focal spot.

BACKGROUND OF THE INVENTION

Such devices are, a.o. used for cosmetic treatment such as e.g. skin rejuvenation including wrinkle treatment and for grooming. In skin treatment, the device is used to create a focal spot in a dermis layer of the skin to be treated without substantially affecting the epidermis layer. The power and pulse duration of the laser and the dimension of the focal spot are selected such that a laser induced optical breakdown (LIOB) phenomenon affects the skin in order to stimulate re-growth of skin tissue and, therewith, to cause skin rejuvenation such as e.g. reduction of wrinkles. An example of such device is disclosed in the international patent application published as WO2008/001284.

With grooming, the device is used to focus the light inside a hair and the LIOB phenomenon causes the hair to be cut through. For example, the international patent application published as WO2005/011510 describes a device for shortening hairs. A dimension of the focal spot and a power of the generated laser beam are such that in the focal spot the laser beam has a power density which is above a characteristic threshold value for hair tissue above which the LIOB phenomenon occurs.

In general, laser induced optical breakdown (LIOB) occurs in media, which are substantially transparent or semi-transparent for the wavelength of the laser beam, when the power density ($W/cm^2$) of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon. The LIOB phenomenon can be seen as an adiabatic expansion effect where all energy is used for expansion of the medium. As such, the device of the invention needs to be distinguished from devices that base their function on direct heating of a medium by laser light. Power densities and laser conditions are generally not comparable.

Hair tissue is transparent or semi-transparent for wavelengths between approximately 500 nm and 2000 nm. For each value of the wavelength within this range, LIOB phenomena occur in the hair tissue at the location of the focal spot when the power density ($W/cm^2$) of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density decreases when the pulse time increases.

In order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ W/cm$\times^2$. For the described pulse time and with a sufficiently small dimension of the focal spot obtained, for example, by means of a lens having a sufficiently large numerical aperture, this threshold value can be achieved with a total pulse energy of only a few tenths of a milliJoule. Parameter values of similar order can be used to generate the LIOB effect in skin tissue as described in WO2008/001284 in more detail.

The effectiveness of optical breakdown for skin rejuvenation depends on several factors such as optical and structural properties of the skin, laser intensity in the focus, optical coupling etc.

The treatment requires scanning of the LIOB focus across an area of tissue.

SUMMARY OF THE INVENTION

There are difficulties in scanning a large surface area at a sufficiently high rate so that treatment time per area is generally high.

It is an object of the invention to at least partly overcome these difficulties. The object is achieved with the invention as defined by the independent claims. The dependent claims provide advantageous embodiments.

Examples in accordance with a first aspect of the invention provide a device adapted to generate laser induced optical breakdown in mammal tissue, the device comprising:
a light source adapted to provide a pulsed light beam;
a beam scanner adapted to provide a scanning pulsed light beam;
a beam focusing unit adapted to focus the scanning pulsed light beam into a focal spot for positioning in the mammal tissue to cause the laser induced optical breakdown,
wherein the beam scanner is adapted to provide the scanning pulsed light beam such that during the scanning of the pulsed light beam a point of intersect of the scanning pulsed light beam and an imaginary plane moves along an arc path lying within the imaginary plane.

The design of the objective lenses in the system makes post-objective scanning and likely also pre-objective scanning of light (beams) difficult if not impossible. Hence scanning the objective itself (i.e. the whole optical assembly) over the intended area is a preferred solution to address a large surface area at sufficient rate.

This system uses a rotating optical parts to implement tracing of the light beam along a path. In this way, high movement speeds of the beam along a tissue surface (e.g. over the skin) are possible because the jerkiness of changing linear scanning direction and the required accelerations and decelerations are largely reduced or even avoided. The invention can make use of the fact that reversal of translational moment which is more difficult and brings about more vibrations than reversal of a rotational moment is avoided.

Furthermore, in known systems, the laser has to be turned off during acceleration and deceleration between reversal of scanning directions of the focusing system in order to avoid over exposure of the skin in the extreme parts of the motion, and this may be avoided using the design of the invention. This is especially so when scanning is along a closed loop with substantially constant speed so that no reversals of scanning motion would be needed.

The invention thus makes a more efficient treatment. It also makes that a handpiece including the scanning and optics parts to be used by a user is more controllable, cheaper and/or smaller.

The invention can be used for treatment of tissue of humans or animals. Especially tissue of boundaries of organs or of skin can be treated.

The device may be adapted to move the focusing unit synchronously, or together, with the pulsed light beam along the arc path during the scanning by the beam scanner.

The beam scanner may comprise:

a beam changer adapted to receive the pulsed light beam having a first beam axis and output a changed beam having a second beam axis which does not coincide with the first beam axis; and a rotator mechanism adapted to rotate the beam changing part about a rotation axis such that that the changed beam implements the scanning pulsed light beam.

The rotator mechanism can be for rotating the beam changing part about an axis parallel and preferably coinciding with the light path.

The beam changing part may be adapted to provide the deflected light path to be parallel to the light path and laterally shifted with respect to the light path.

The beam changer can be or comprise a beam deflector or beam refractor.

The beam focusing unit may be coupled to the beam changing part to rotate with the beam changing part. This gives good optical coupling while rotational scanning is implemented.

The beam changing part can be implemented in a number of ways. The beam changing part can comprise one or more surfaces for refracting or reflecting the pulsed light beam. Devices with such surfaces can be mirrors for implementing the change of the light path to the changed light path. This is a light weight solution. Also separate mirrors can be used if multiple such elements are used. These can be moved independently in implementations as with FIG. 4.

The beam changing part can comprise one or more prisms for implementing the change of the light path to the deflected light path. The prism may comprise a rhomboid prism. This makes use of two total internal reflections to provide a Z-shaped beam path through the prism thereby implementing a lateral (i.e. perpendicular to the beam direction) shift in path axis.

The prism may comprise a dove prism. This makes use of two refractions and one total internal reflection to provide a V-shaped beam path (with left-right input and output from the V) through the prism thereby implementing a lateral (i.e. perpendicular to the left-right beam direction) shift in path axis.

These two prism design make use of total internal reflection, which gives a high damage threshold and very low losses. Also, the prism can be rotated as one device for implementing the scanning giving good opportunity for rotational balance and robustness as well as compactness.

In the device the rotator mechanism may be adapted to:

implement full 360 degree rotation of the beam changing part; or implement a back and forth alternating rotation of less than 360 degrees of the beam changing part. For example, the method may implement full 360 degree rotation of the prism/mirror or an alternating rotation of less than 360 degrees of the prism/mirror. The rotation system enables a large surface area to be scanned at a sufficiently high rate. The system is able to follow skin contours and to accommodate for the skin local curvature and to exert pressure on the skin. The system is able to have a relatively high aspect ratio and at the same time demonstrate significant performance with respect to contour following.

A device as claimed in any of claims 3 to 9, the first beam axis and the second beam axis defining a distance measured perpendicularly to the first beam axis, and comprising a further mechanism for changing the distance.

Adjustable arc path radius can herewith be implemented. The adjustability can be manual or motorized either between use (a scanning session) of the device or during use Hence areas of scanning can be set according to need by a user.

The further mechanism can comprise that the beam changer includes:

one or more beam refractive or reflective surfaces at least one of which can be tilted with regard to the first beam axis, or at least two beam refractive or reflective surfaces between which a distance can be changed.

Tilting of a surface which changes the direction of the beam axis may be a convenient and small form factor way to implement change of radius of arc path. For example, a reflective surface used to turn beam axis 31 into 34 can be tilted to increase the angel between 34 and 32 so that distance 36 increases. This principle can also be used in the implementation of FIG. 4.

Increasing for example the distance along direction 42 between two reflective surfaces, one used to turn axis 42 into axis 44 and another to turn axis 44 into 47, will lead to increase of distance 46. This mechanism may only need a sliding of units along the axis 42 which can be manual or motorized.

The focusing system can comprise:

a pre-focusing lens for increasing the convergence of the scanning pulsed light beam; and a focusing lens having convex light input and light exit surfaces. The focusing lens can be surface contact lens (e.g. tissue surface lens). Alternatively, there may be another exit window behind which the focusing lens is situated.

This arrangement provides a focusing system which gives a controllable depth, even during use if desired.

The pre-focusing lens may comprise an aspheric lens.

The pre-focusing lens may comprise:

a convex light input surface; and a planar light output surface or a convex light output surface with an average radius of curvature greater than the average radius of curvature of the light input surface.

The skin contact lens may be formed of BK7 glass or fused silica.

The outer surface of the skin contact lens for contacting the skin preferably comprises an anti-reflection coating. This prevents damage to the focusing system itself from reflected light from the skin.

In one arrangement, the device further comprises an electrically adjustable lens system before the beam scanning system for providing compensation for aberration in the focusing system. This enables the LIOB efficiency to be maintained at different focal depths.

In a first example, the adjustable lens system comprises an electrically tunable polymer lens. The adjustable lens system may then further comprise a negative lens at the output of the electrically tunable polymer lens. This negative lens provides compensation for the initial shape of the polymer lens.

In a second example, the adjustable lens system comprises an electrowetting lens.

The device may comprising a focus controller for controlling the distance from the focusing system to the focal spot by adjusting a spacing between the pre-focusing lens and the focusing lens.

The device can comprise:
a beam compressor part (90) arranged before the beam scanner (92); and
a beam expander part (40) after the beam scanner 92;
Beam compression may be provided before the beam scanning and providing beam expanding may be provided after the beam scanning.

A device as claimed in any preceding claim, further comprising an adjustable lens system arranged in the light path before the beam scanning system for providing compensation for aberration in the focusing system. This is especially useful when the focusing system provides for adjustable focus depth. Each depth may require different aberration compensation in order to create optimum focus quality.

The invention also provides a light based skin treatment method comprising:
providing a pulsed incident light beam for treating skin by laser induced optical breakdown of hair or skin tissue;
scanning the beam to define a circular or arc path using a prism which implements a lateral shift to the beam by rotating the prism about an incident axis along which the light beam incident to the prism passes; and
focusing the incident light beam into a focal spot in the hair or skin tissue, wherein the focusing system rotates with the prism.

This method is a non-therapeutic method, in particular a cosmetic methods, for skin rejuvenation or hair removal. The method can be used to change the appearance of skin for example with regard to pigmentation, relief (wrinkle reduction).

BRIEF DESCRIPTION OF THE DRAWINGS

Examples of the invention will now be described in detail with reference to the accompanying schematic drawings, in which:

FIG. 2A to 2D. show examples of arc paths followed by the scanning of the beam as implemented with the invention;

FIGS. 5A to 5D show prisms for implementing lateral beam shift with e.g. implementation of FIG. 4. It also shows beam expansion and extreme focusing positions;

DETAILED DESCRIPTION OF THE EMBODIMENTS

This invention relates to device for generating laser induced optical breakdown (LIOB) in tissue. It can for example be a skin treatment device for (cosmetic) treatment of skin of mammals such as humans or animals. The device comprises a light source (usually and preferably a laser) for providing a light beam with an intensity that is suitable for causing the LIOB in the tissue, at least when the light beam is focused in the tissue. To this end the system includes a focusing system for creating a focused light beam defining a focus located outside the focusing system such that by manipulating the focusing system the focus can be positioned in the tissue to be treated. Preferably the focus can thus be positioned below a surface of the tissue to be treated.

The device also includes a beam scanning system that is adapted to scan the focused beam along a curved path over a surface of the tissue to be treated. This system and kind of scanning ensures a smooth movement of the focal spot underneath and along the surface of the tissue while a sufficient scan rate of a predetermined surface area can be achieved.

The scanning system can be implemented in many ways according to the invention a number of which will be described herein below. However, before describing the invention in detail, an outline will be given of one example of the type of device to which the invention relates which is for cosmetic treatment of skin. A device for grooming purposes or other purposes of treatment of tissue can be constructed in a largely similar way.

Figure 1:
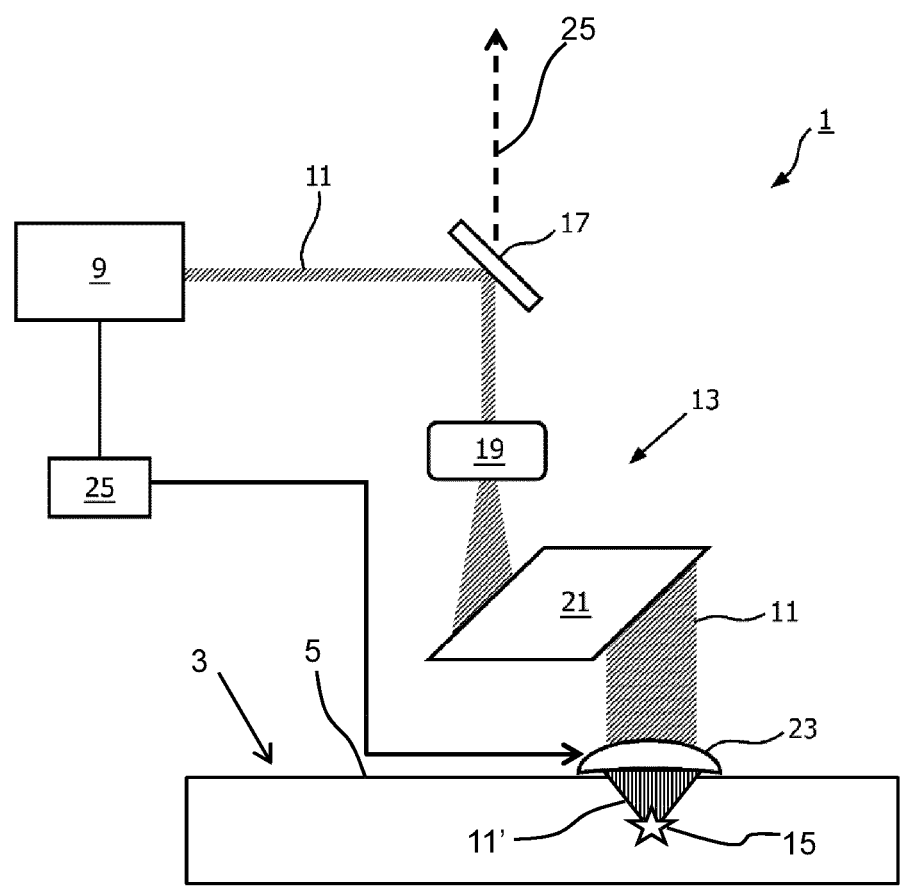
FIG. 1 schematically shows a LIOB treatment device.

The device 1 in FIG. 1 is situated for treatment of a tissue (in this example skin) 3 having a tissue surface (e.g. outer surface of epidermis) 5.

The device comprises a light source 9, which in this example is a laser for generating a pulsed laser beam 11 and an optical system 13 for manipulating and focusing the laser beam 11 into a focused laser beam 11' which is focused in a focal spot 15.

The skin 3 of a mammal (e.g. human) comprises multiple layers with different optical properties. The epidermis is composed of the outermost layers and forms a waterproof protective barrier. Underneath the epidermis, the dermis is situated which comprises the collagen fibers at which the treatment with device 1 is aimed. The purpose of the skin treatment and the device of the invention is to create the focus 15 of the pulsed laser beam 11 in the collagen of the dermis in order to create microscopic lesions while leaving the epidermis largely unaffected. The lesions may result in new collagen formation and therewith a skin rejuvenation such as for example wrinkle reduction may be achieved.

The optical system, and focusing system, of the device 1 is thus designed such that the focal spot 15 can be positioned in a target position within the skin 3 below the surface 5. Hence the focusing system is designed such that the focal spot lies outside the focusing system and at a certain distance from the exit window/lens of the system. The dimension of the focal spot 15 and the power of the generated laser beam are such that, in the focal spot 15, the laser beam 11 has a power density, which is above the characteristic threshold value for the skin tissue, above which, for the predetermined pulse time, a laser-induced optical breakdown (LIOB) event can occur. The focusing system is also designed such that even with light energies capable of causing the LIOB, the epidermis is left largely unaffected.

The light source is adapted to provide a laser beam with a wavelength or wavelength range such that the skin surface is at least partly and preferably substantially transparent and non-scattering to the light from the light source. This enables suitable penetration depth of the light into the skin of up to e.g. 3 mm. The light source is also adapted to provide enough energy per pulse to cause the LIOB phenomenon in the tissue at the focal spot. A 1064 nm wavelength laser is a preferred laser type, but others can be used. Thus, in this example the light source comprises a Q-switched Nd:YAG laser emitting laser pulses at a wavelength of about 1064 nm with a pulse duration of about 5-10 ns. However, as said, other lasers known in the art, such as e.g. a Nd:Cr:Yag 3-level laser and/or diode lasers may be used.

The example of the optical system 13 comprises further optical elements for manipulating the laser beam 11, but these may not all be necessary for implementing the invention as will be explained below. Thus, the device 1 also includes a beam reflecting system 17, a beam shaping system 19, a focusing system 23, which systems may comprise one or more mirrors, prisms, beam splitters, polarizers, optical fibers, lenses, apertures, shutters, etc. for manipulating the light of the laser beam 11.

The beam reflecting system 17 in this case is a dichroic beam splitter, but others can be used. The beam reflecting and beam shaping system provide expanding or compressing of the beam, to introduce additional convergence or divergence to the beam where necessary.

The focusing system in this case is a high NA lens system having one or more lenses. Laser beam focusing parameters may be determined by appropriate settings of a beam shaping and/or focusing system, e.g. by adjustment of the numerical aperture of the focusing system. Suitable values for the numerical aperture NA of the focusing system may be chosen from a range 0.05<NA<nm, wherein nm is the index of refraction of the medium for the laser wavelength, during operation.

At least part of the optical system 13 and/or the beam path of the laser beam 11 may be enclosed in a light tight enclosure, e.g. for eye-safety, e.g. comprising opaque tubes and/or one or more optical fibers.

The optical system also includes a beam scanning system 21 which is designed for manipulating the beam 11 such that the focused beam 11' and therewith the focal spot 15 can be scanned along the surface 5 of the skin 3 in order to treat an area of the skin during use of the device 1. The scanning system 21 can comprises scanning prisms to this end.

The scanning systems of prior art devices have been designed for back and forth scanning along a linear trajectory. This design and way of scanning can cause difficulties during use of the device as will be explained below.

For example, the light source 9 is configured to emit a predetermined number of laser pulses and with a predetermined pulse duration (in this case ~5 to 10 ns) and pulse repetition rate (a pulse repetition frequency) of e.g. 1000 Hz. Because a typical LIOB lesion diameter can be in the order of 200 micrometer or smaller, a typical lesion pitch of at least in the order of 200 μm would be needed to prevent lesion overlap during a treatment. Thus, a treatment regime (method) that uses less than 100% area treatment of a skin would need a scan speed of already 200 mm/s.

This scan speed rules out any manual-scanning-only options because of lack of control when applying these rather high scanning speeds by hand. Additionally, any start-stop scanning system or forward-reverse scanning system will be severely challenged to reach this scanning speed over a short distance of acceleration, leading to mechanical vibrations and ineffective use of the capacity of the light source (e.g. laser). Furthermore, in such systems, the laser has to be turned off during acceleration and deceleration of the focusing system in order to avoid over exposure of the skin. On the other hand, a more easily controlled slower scanning speed (together with a lower laser pulse repetition rate) will lead to an undesired significantly increased treatment time for surface areas typically treated.

To overcome all this, the invention makes use of a continuous motion scanning along a curved path or trajectory avoiding sharp turns or linear movement reversals. The device, and especially the scanning system in combination with the focussing system are adapted to implement such scanning. With such smooth trajectory scanning increased scan speeds can be obtained without suffering from strong vibrations and ineffective use of the laser capabilities. This increased scanning in turn allows slower manual manipulation with comcomittant improved control while still providing acceptable treatment times for an area to be treated.

FIGS. 2A and 2B Show some preferred examples of closed loop paths or trajectories along which laser pulses are provided suitable for use with the invention. FIGS. 2A and 2B shows a circular 20 and elliptic 21 path respectively. However, other paths can be used such as spirals (circular with increasing or decreasing radius). Depending on the speed of travel of the focal point along the trajectory and the laser repetition rate, multiple LIOB events (represented by stars) occur at predetermined mutual distance along the trajectory 20 or 21. Thus, the trajectory is sampled with LIOB events as it were. The mutual distance can be set by the laser pulse repetition rate in combination with scanning speed. FIGS. 2C and D show how translation along directions 22 and 23 can be used to cover an area of treatment. In this drawing a closed loop trajectory is scanned after which the scanning center (for example by moving the focusing system) is translated to provide the second scan etc. In practice however, the translation and scanning can be continuous such that the circles or ellipses will be replaced with a continuous repeating motion resembling the FIGS. 2C and D. Thus, the shape of the trajectory together with direction of translation determines a shape of an area to be treated. While with a circular trajectory such area shape (treatment area band with width equal to diameter of circle) is independent of translation direction 22, because of the circular symmetry, this is not so for e.g. the elliptical trajectory. The latter one provides a treatment area that is broader when translating in direction 22 in comparison to translation in direction 23. This can be advantageous when narrow and broad areas need to be treated. The same effect can be obtained using circular translation, but then the diameter (radius of the circle must be adjusted, possibly in combination with LIOB repetition distance along the trajectory in order to keep the same LIOB area density over a surface.

Thus, fast rotation can be used together with better controllable less fast translation to cover an area while pulse repetition frequency can be kept relatively high to ensure sufficient lesion density over the area. Of course, the rotation speed, radius of rotation and/or pulse repetition rate can be adjusted to correct for differences in radius so that still the density of lesions (one per pulse) is evenly distributed along the spiral trajectory.

As an example of indications of scanning and translation speeds the following may be considered. There is a minimum rotation speed associated to the pulse repetition rate of the laser and the size of the generated lesions. Considering a lesion size of e.g. 100 micrometer and a laser pulse rate of 1000 Hz. The motion along the scanning trajectory (linear in prior art) should then be at least 100 mm/s in order to avoid overlapping lesions. As an example, with a device head of 1.5 cm cross section with circular scanning of the beam (focus) at a radius of ~0.75 cm, a rotation speed of approximately 2 full turns per second or faster would be needed to achieve such speeds. The speed of manual motion for the translation should then be at least 0.2 mm/s again in order to prevent overlap. This would imply 100% coverage (which would likely be too high for a single treatment). More probably, the manual motion would be faster (e.g. 2-5 mm/s) whereas typical lesion sizes could be smaller (e.g. >50 micrometer) depending on the laser energy and treatment depth. To reach 10% coverage (in a single pass one would use e.g. a rotation speed of ~6 turns per second and a manual motion of ~0.5-1.5 mm/s, preferably, 0.6 to 1.2 mm/s. These figures scale linearly with laser pulse frequency. With such parameters a treatment of an area of 100 cm$^2$ with 10% LIOB lesion density will take approximately 7.5 minutes. But note that decreasing the pulse frequency causes decrease of translational motion in order to maintain coverage in single pass. Hence total treatment time of an area increases.

In FIG. 2A there are LIOB events along the entire closed loop path. However, with scanning of FIG. 2C, this would mean that double LIOB events can take place in one spot due to the translation. To circumvent this the light source can be shut off or blocked using a shutter for example for at least a part of the curve. FIG. 2B shows LIOB events to occur on only one half of the scanning path. Scanning in direction 22 now will not give overlap of LIOB events.

According to the invention, the scanning system is adapted to provide beam scanning or manipulation to implement the smooth scanning of focus over the area. The beam scanning system of e.g. the device of FIG. 1 can be replaced with one according to the invention. Different implementations will be described herein below.

Figure 3:
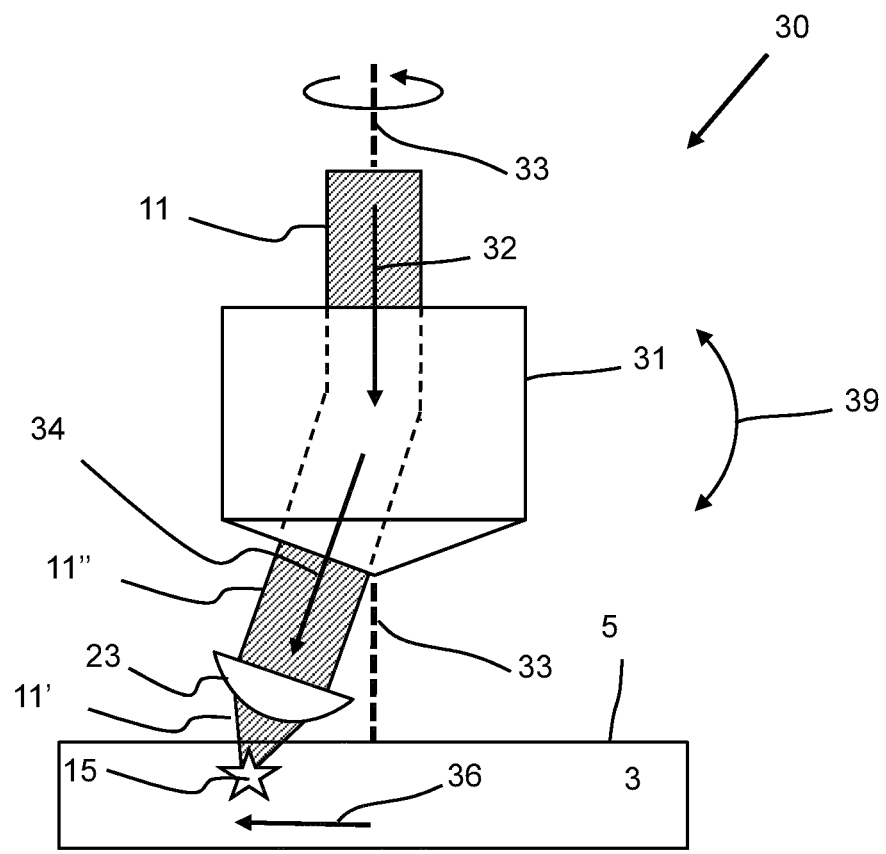
FIG. 3 shows a first implementation of arc path beam scanning.

FIG. 3 shows a first design of a scanning system to provide this implementation. The beam scanning system 30 includes an optical device 31 for receiving and manipulating the pulsed light beam 11 coming from the light source and which enters the optical device along a first direction 32. The optical device 31 is adapted to change the first direction 32 into second direction 34 that is different form the first direction so that a redirected pulsed light beam 11" exits the optical device 31. The redirected pulsed light beam 11" is focused by focusing system 23 into focal beam 11' with focal spot 15. As described before, during use, the focal spot 15 is positioned in the tissue 3 beneath tissue surface 5. In this example, the optical device 31 rotates together (in sync) with focusing system 23 about axis 33. As a consequence, the focused beam 11' and the focal spot 15 also rotate about the axis and therewith implement the rotational trajectory across the surface 5 (see e.g. FIGS. 2A to 2D). The focal spot rotates with radius 36 about the axis. This radius may correspond with the 0.75 cm of the device head mentioned in relation to FIG. 2. During the rotation the radius may be constant to implement trajectories as in FIG. 2A, but alternatively, the radius may vary between ultimate values for example to implement trajectories such as those of FIG. 2B. Hereinabove. Manual or mechanical translation of the location of the translation axis across the surface can now be used to with good control cover treatment of an area as explained with reference to FIG. 2.

In this example, the lens system 23 is slightly tilted to accommodate the skewed direction 34 (skewed with regard to direction 32). This need not always be the case, but is preferred for most efficient focusing.

The beam 11 is drawn as parallel beam, this need however not be the case for implementation of the invention. A converging or diverging beam may be redirected with good effect as long as good focusing can be achieved afterwards.

The optical device 31 can comprise or consist of one or more mirrors for redirecting the pulsed beam 11. Alternatively, or additionally one or more prisms (e.g. triangular ones) can be used. Preferably elements are used that do not result in loss of light i.e. that work based on total (internal reflection) so that all light is eventually redirected into direction 34. Prism can be used for this purpose.

In the example of FIG. 3, the focusing system 23 rotates in sync with the scanning system. It may be thus mounted on an independent rotator that is driven in sync with the rotation of the optical device 31. However, it is easier to fix it to the rotating mechanism of the optical device 31. This provides a simple way of good stable optical alignment between the focusing system and scanning system, which is of importance as high energies are used and focus depth control must be precise. However, it does imply that there is a focusing system sweeping over the surface of the skin. An alternative that would prevent such sweeping is one where the focusing system comprises more than two, and preferably a larger plurality of lenses along the focused beam 11' rotation trajectory. Referring to FIG. 2A, for example the amount of lenses equal to the desired amount of LIOB events (stars) could be chosen such that a rotational motion can be drawn. A minimum of three lenses should be used then. These lenses do not need to rotate with the scanning system as long as the rotation of the beam and the pulse repetition rate is chosen such that every time that a next laser beam pulse arrives, the scanning system is lined up with one of, and preferably the next or later, lens in line. This would require a rotation frequency that is the pulse frequency divided by a multiple of the number of lenses for example. A feedback system can be used for correct alignment. The focusing system rotating with the scanning system is however preferred.

Figure 4:
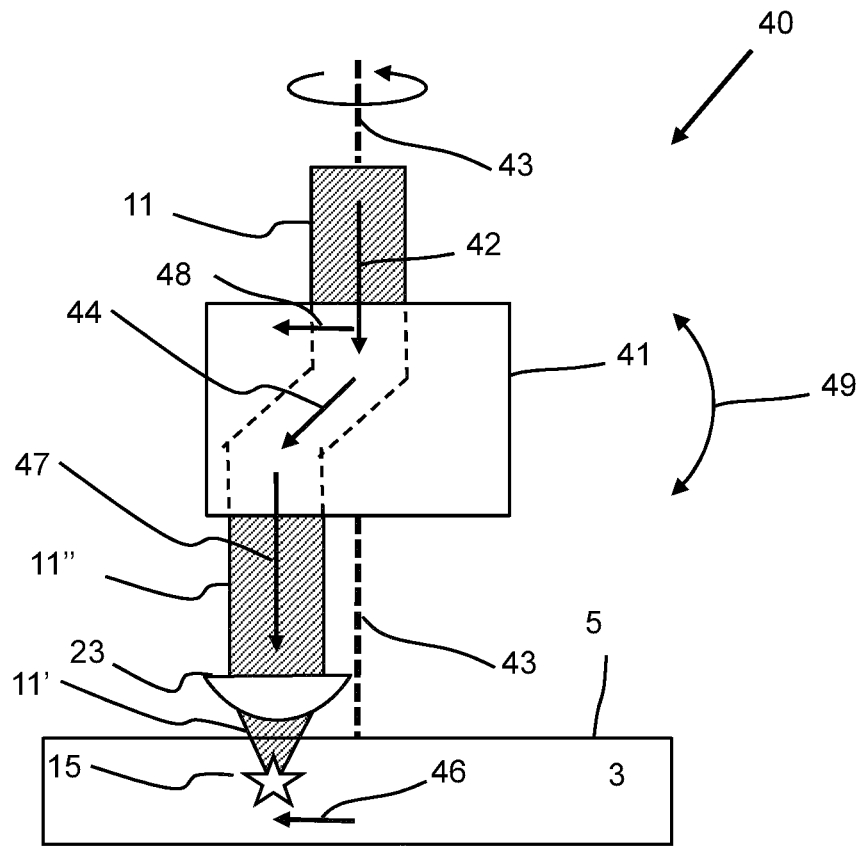
FIG. 4 shows a second implementation of arc path beam scanning.

It may be preferred that the focussing system and in particular its exit lens is placed on the surface with its lens axis vertical (not tilted) to the surface for giving smooth movement over a surface that may be non-flat while still good focus depth control is achieved. FIG. 4 shows an scanning system to implement that. Thus, the beam scanning system 40 includes an optical device 41 for receiving and manipulating the pulsed light beam 11 which enters the optical device along a first direction 42. The optical device 41 is adapted to change the first direction 42 into second direction 44 which is different than the first direction. However, before leaving the optical device 41, the beam with the second direction 44 is redirected another time into a third direction 47 which, in this case is parallel to the first direction 42, so that a pulsed light beam 11" exits the optical device 41, which beam laterally translated or shifted with respect to beam 11 entering the optical device 41. The shift occurs along direction 48 which may be vertical to the rotation axis 43 and the first direction 42 of beam 11. The shifted pulsed light beam 11" is subsequently focused by focusing system 23 into focal beam 11' with focal spot 15.

As described before, during use of a device having this scanning system, the focal spot 15 is positioned in the tissue 3 beneath tissue surface 5. In this example, the optical device 41 rotates again together (in sync) with focusing system 23 about axis 43. As a consequence, the focused beam 11' and the focal spot 15 also rotate about the axis and therewith implement the rotational trajectory across the surface 5 (see e.g. FIG. 2). The focal spot rotates with radius 46 about the axis 43. Manual or mechanical translation of the location of the translation axis across the surface can now be used to with good control cover treatment of an area as explained with reference to FIG. 2. Use of the scanning system can be similar to that described with the example of FIG. 3.

In comparison with the scanning system of FIG. 3, the one of FIG. 4 results in that the lens axis of the exit lens of the focussing system is vertical to the surface. This can be the case since the optical device is designed such that the third direction 47 of beam 11" is such that the beam 11 is parallel with beam 11", but is at least partly non-coinciding. However, in FIG. 4, the beam does not need to be parallel for the invention to be implemented and can be skewed with regard to the vertical to surface 5. This would again lead to a situation as with FIG. 3.

If the beams of FIG. 3 or 4 were skewed, then a convex contact window could be used against which the skin would be pressed and on the inner side of which the lens would rotate.

In the optical device of FIG. 4, mirrors can be used for redirecting the beam. Alternatively, prisms can be used. Again total internal reflection elements are preferred.

The scanning systems 30 and 40 can be adapted to allow change of rotation radius 36 or 46 between use sessions or continuously. One way of doing this is to implement a mechanism that allows tilt 39 or 49 through e.g. pivoting of the optical device 31 or 41 so that direction 34 or 47 tilts accordingly. Alternatively, and preferably if the beam 47 is to be kept with the same direction for different radii 46, the optical device 41 can be adapted to allow change of the lateral translation 48. This could for example be done by increasing the distance measured along the direction 42 between the elements for the first redirection and the second redirection of the beam so that the beam 11 travels for a longer distance along direction 44. Mutually shiftable mirrors or prisms can be used for that. Such distance manipulation can be manual or motor controlled via example equipment software etc. Other variations can be used without loss of the radius adaptability.

FIG. 5A shows a first design according to FIG. 4 based on a rhomboid prism 50 as part of the optical device. Two opposite parallel end faces 50a, 50b function as total internal reflection faces. They are at 45 degrees to the incident light direction coinciding with the first direction 42 of pulsed light beam 11. The two internal reflections in the prism provide a lateral shift of the incident beam 11, so that exit beam 11" is parallel but laterally shifted relative to the input beam. By rotating the prism about an axis perpendicular to the lateral shift direction, and therefore parallel to the incident beam direction a circular path is swept by the output beam 11". The rotation is about the axis of the input beam 11. The radius of the circle swept is the length of the rhomboid. Rhomboid prisms can be manufactured with anti-reflection coatings on the faces where required.

FIG. 5B shows a second prism design. The design comprises a dove prism 52. The two end faces 52a, 52b function as refraction interfaces, and the bottom face 52c functions as a total internal reflection face. The end faces are at 45 degrees to the incident light. The two refractions and the single total internal reflection in the prism again provide a lateral shift of an incident beam, so that exit beam is parallel but laterally shifted relative to the input beam. By rotating the prism about an axis perpendicular to the lateral shift direction, and therefore parallel to the incident beam direction, a circular path is swept by the output beam. The rotation is about the axis of the input beam. The amount of beam translation depends on the position of the incident beam relative to the input surface 52a of the dove prism and on the size of the prism. The prism is rotated around the chief incident ray. Anti-reflection coatings may again be added on the angled surfaces to reduce losses by reflection.

The use of a rotating prism as with the embodiments of FIG. 5 avoid alignment issues, reduces the risk of optical damage and has reduced stability related issues associated with deflection based on coated mirrors.

There are many other prism designs which could be used. However, the two designs described above are particularly useful because they employ total internal reflection. Especially in this case where LIOB requires high energy density light beams it is beneficial to use the total internal reflection and associated high damage threshold and very low losses, making these designs particularly useful for this application where high energy density light is used.

The rhomboid prism has a minimum beam displacement equal to the total aperture of the rhomboid. However, the dove prism can virtually overlap the incident and emitted beam, allowing for smaller scan radius than the rhomboid, and additionally the actual amount of beam displacement is tunable even after the prism has been manufactured by selecting the position of the input light beam relative to the dove prism shape.

The benefit of the rhomboid is that, apart from polarization disturbance at the total internal reflection surfaces, it is optically represented by a thick slab of glass, reducing the influence of the prism on aberrations in convergent and divergent beams. Furthermore, for a given amount of beam displacement and clear aperture, the rhomboid has lower minimum weight since the length of the Dove prism typically needs to be approximately four times the cross section of the clear aperture.

The prism has an associated weight, which should be kept to a minimum, e.g. for balancing purposes during rotation. For this purpose, the beam is expanded just after deflection by the prism using a combination of a plano-concave lens (e.g. f=12.0 mm) and a plano-convex lens (e.g. f=30 mm) which together form the expander lens 40 resulting in a beam expansion of 2.5 times. In this way the beam diameter passing through the prism can be kept relatively small, allowing for small size prisms.

As said hereinbefore, mirrors can be used, but using mirrors with this high intensity light would require specialized high reflecting coatings and substrates for a mirror, whereas the rhomboid prism would rely solely on total internal reflections, requiring perhaps only simple anti reflection coatings on the entry and exit surfaces of the prism.

Other devices for deflecting beams are acousto/electro optics, Liquid crystals etc, but these tend to be expensive, lossy, and/or prone to laser damage.

The scanning system or the rotating part of the scanning system such as the rotating prisms is preferably mechanically balanced to avoid vibration. To this end the rotating parts may be arranged and/or adapted, with or without additional weight balancing, such that the axis of rotation coincides with an axis of inertia of the rotating parts. A mount for rotating the necessary parts can be suspended on ball bearings and connects directly to a motor rotor so as to minimize the influence of the aberration correction settings on the effective numerical aperture of the focused light. Other types of balancing may however be used and other methods of supporting smooth motion such as e.g. magnetic bearing or fluid bearing can also be used.

FIG. 5A shows ray paths through the rhomboid prism 50, through a diverging beam expander lens 56 (e.g. 2.5 times) and the focusing system 23. FIG. 4(*b*) shows ray paths through the dove prism 52, through a diverging beam expander lens 56 and the focusing system 23. Note that the focusing system 23 is shown as comprising a pair of lenses. This double lens design is not per se needed for the invention to work, but can give good focusing.

To accommodate scanning of small areas the rotary scanning may be implemented in an alternating fashion, while the treatment rate is automatically adapted to the instantaneous speed of the scanner. Thus, continuous one direction rotation is then switched to back and forth rotation over only part of the total rotation the device. Alternatively, the rotation can be kept continuous, but the laser is turned off or blocked using a shutter or diaphragm so that it provides only pulses to the skin along a predetermined smaller part of the scanning curve. For example as depicted in FIG. 2B, where the scanning continues over the closed loop, but LIOB pulses are only provided during half of the loop. Other defined loop segments can be set as required by the area to be treated. Thus, in such embodiments of the invention the device is also capable of performing forward backward scanning, but along the curved path. Vibrations associated with back and forth rotational movement is far less than vibrations caused by linear back and forth movement.

An alternating scanning approach can be based on any start-stop scanning system which reaches the required scanning speed over a short distance of acceleration while the treatment rate (defined by the size of the small treatment window) is automatically adapted. One implementation is based on the design of CD/DVD optics having a split optics approach with mechanical scanning of a lens using stepper motor drives.

Figure 6:
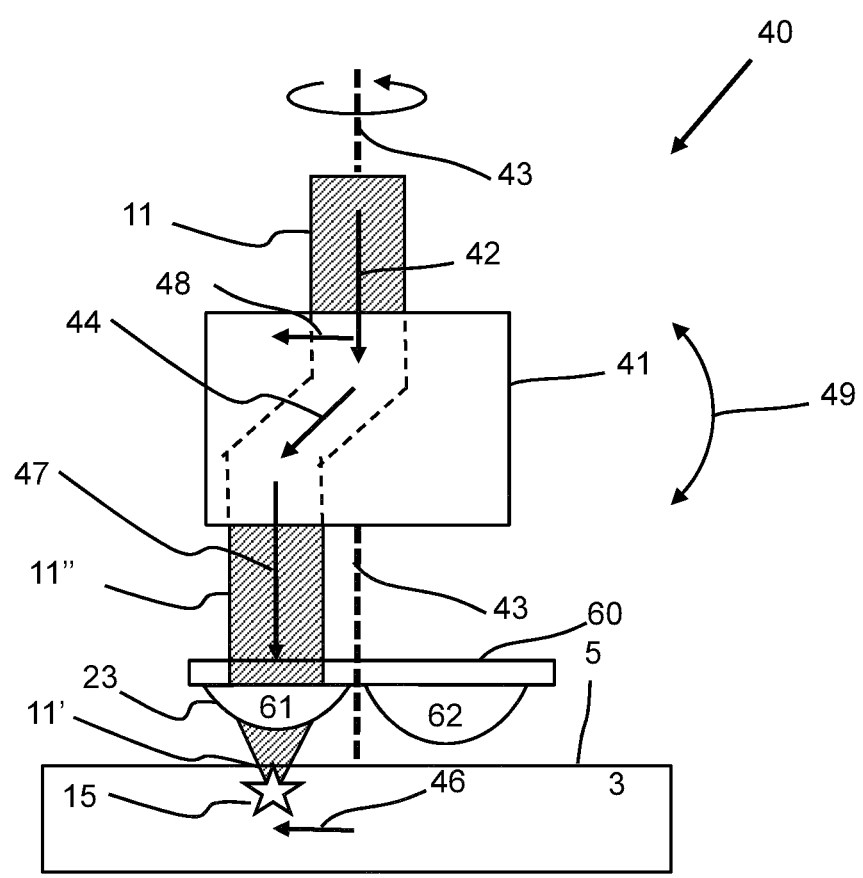
FIG. 6. Shows a lens carousel for implementing different focus depth positions.

FIG. 6 shows a way to implement focus depth adjustment using a focusing system with lenses 61 and 62 mounted on a holder 60. In this example two lenses are shown, but more than two can be used. Each of the lenses provides a different focus depth. The mount 60 and the lenses in this case rotate with the scanner around axis 43 during scanning. If lens 61 needs to be replaced with lens 62, the mount 60 is rotated with regard to device 41. The lenses are thus arranged around a circular path, and a notch system provides positioning with respect to the scanning system 21. Other clamp mechanism can be used to rotate during exchange of lenses while fixing the lens during scanning with the device. Other ways of adjustable fixing of lenses in the path can be used. The adjustment can be manual, but also motorized and controlled with a controller, for example controller 25.

The focusing system, or a lens part of it and or the scanning system preferably are held by a surface contour following suspension system which allows an exit window, lens or multiple of those to be together or separately spring loaded to provide contour following during rotation scanning and/or translation when the device is used. Especially with contact mode scanning of the device this is advantageous in keeping the contact in place while scanning relief surfaces such as skin and minimizing discomfort.

Figure 7A:
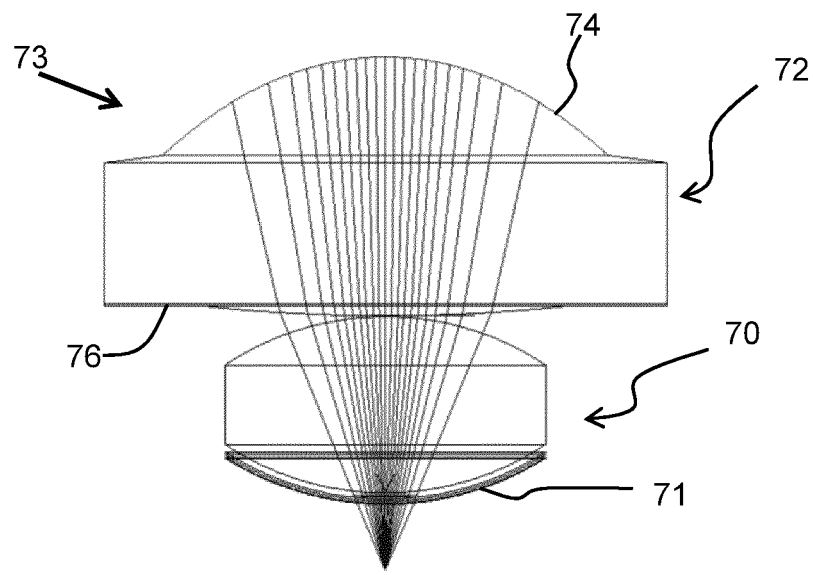
FIGS. 7A to 7C show a focusing system with adjustable focus by lens distance change.
Figures 7B, 7C:
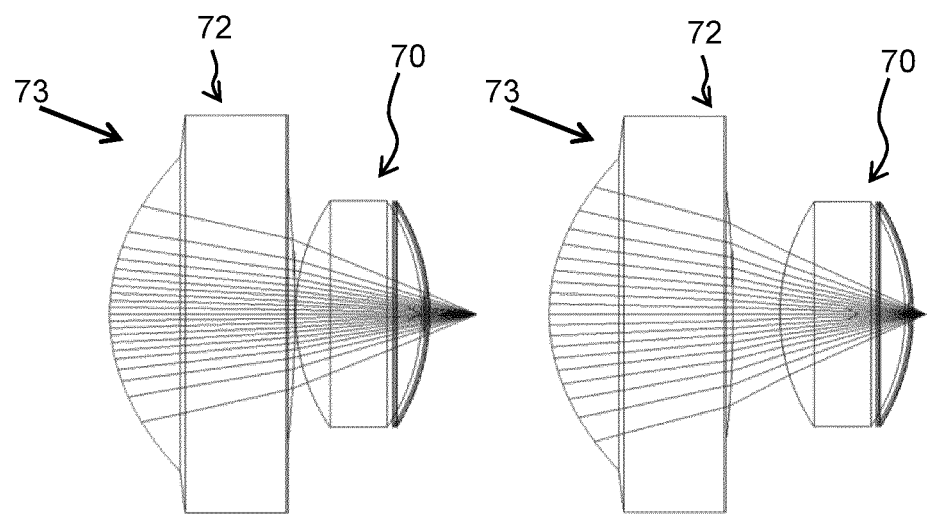

An alternative way of implementing multiple depth focusing in combination with the scanning of the invention is described in relation to FIGS. 7A to 7C in which the focusing system 23 is shown as a pair of lenses. For example, FIGS. 5C and 5D show the location of such focusing system 23 with regard to prisms of a scanning system. The double lens system enables the focal position to be adjusted while also providing optimal skin coupling. The double lens system can rotate with the scanning system and the plurality of lenses of the multifocal solution of FIG. 6 can be avoided. Also the system of FIGS. 7A to C can provide continuously controlled focal depth.

The detailed design of the focusing system with the multiple lenses has been described in non-pre-published European patent application 16183299.3 which is incorporated by reference and the system will only be briefly described herein below for that reason.

Thus, the focusing system comprises the combination of an output lens 70 and a pre-focusing lens 72.

The lens 70 is manufactured from an optical glass, such as with Abbe number in the range 50 to 85. For example, the borosilicate Crown glass known as BK7 may be used. Alternatively, a Fused Silica lens may be used. Others could be used, but these perform well. The materials are generally transparent to the wavelength to be transmitted (e.g. the 1064 nm light of the Nd:YAG source) with a high damage threshold. The lens 70 comprises a bi-convex lens, for example a fused silica bi-convex lens with anti-reflection coatings 71 on both sides of the output part of the lens, suitable for the 1064 nm high power laser.

The lenses on each side of the structure have the same curvature and design.

The lens 72 comprises a commercially available aspheric lens already used in used and known to be able to sustain the laser intensity. The purpose of the lens 72 is to convert near collimated light coming from the scanning system (see FIG. 1) into a desired convergence angle.

Suitable aspheric lenses are known for use with laser diodes, photodiodes and fiber coupling systems, and in the field of optical data recording. By way of example, suitable lenses are manufactured by LightPath Technologies Inc.

The lens 72 has a convex light input surface 74 and a planar light exit surface 76 or else a convex light exit surface 76 with a lens surface with greater radius of curvature than the light input surface.

The spacing between the two lenses 70, 72 is adjustable to vary the focal depth. Thus, there is a control path between the controller 25 of a device according to the invention and the focusing system 23 as shown in FIG. 1. The adjustment is shown in FIGS. 7B and 7C. Movement between the lenses may for example be controlled between a set of fixed focusing depths or continuously either manually or based on feedback.

FIG. 7B shows a first zero spacing between the two lenses, which corresponds to a maximum focal depth for example of around 750 micrometer. FIG. 7C shows a maximum spacing between the two lenses, which corresponds to a minimum focal depth for example of around 200 micrometer.

The combination of the two lenses introduces some limitations with respect to the user specification. This is related to the limited free working distance of the aspheric lens 72, combined with the limitations on the minimum achievable thickness of the lens 70.

For example, the maximum achievable treatment depth inside the dermis may be limited to approximately 750 micrometer as mentioned above.

As a consequence, the convergence of the light incident on the lens 72 may need to be corrected for this effect, i.e. slightly convergent incidence is required.

The variable focus capability for multiple depth treatment means that some aberration correction may need to be installed to compensate, i.e. the relative shift in distance between the two lenses implies that some aberration correction may need to be installed to compensate. Examples of how to implement this aberration correction are discussed below. A detailed discussion of how to implement the aberration correction is provided in the non-pre-published European patent application 16183301.7 which is incorporated by reference and the system will only be briefly described herein below for that reason.

Thus the aberration correction may be implemented at various points in the light beam of the device of the invention, for example before or after beam shaping (by beam shaping system 19). Furthermore, the beam shaping system 19 may be implemented by the focusing system 23 so that only aberration correction is provided between the beam reflecting system 17 and the scanning system 21.

To correct for the spherical aberration that is expected when focusing at different depths, the divergence of the beam incident on the scanning prisms of the scanning system 21 may be made adjustable. A simplest solution would be to allow the user to adjust the divergence of the beam by manipulating one or more lens positions. However, since the placement of these lenses is quite critical and the system needs to be operable by users without a background in laser optics, it would be better to implement some form of automated correction that adjusts the position or strength of a lens depending on the selected focusing depth, or even on the fly, for example depending on the observed LIOB flash intensity. A second aspect of the invention relates to aberration correction.

Since motorized focusing typically consumes a lot of space and is mechanically complex and typically too slow to accommodate for dynamic variations, an adaptive optical element is preferred. Two examples of suitable adaptive optical element are electrically tunable lenses such as an electrically tunable low dispersion polymer lens controlled by a voice coil motor device, and a liquid focusing lens. See e.g. non-pre-published European patent application 16183301.7 for the details of such lenses.

Figure 8:
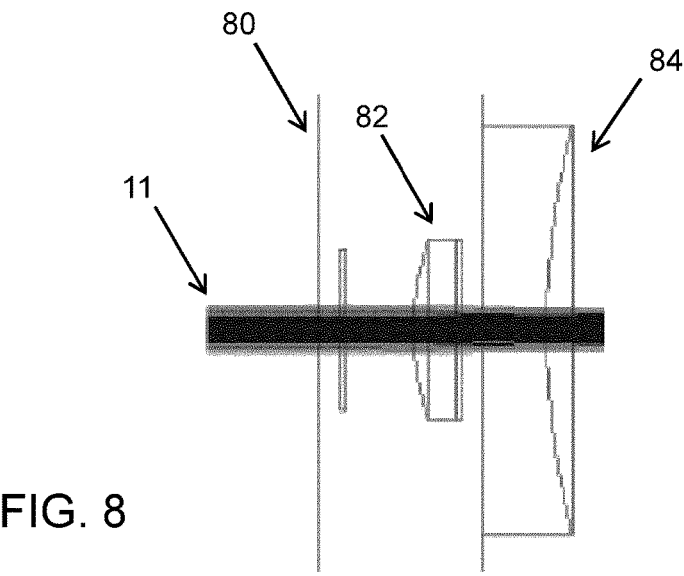
FIG. 8 shows a second example of a lens system for providing aberration compensation.

FIG. 8 shows a variable lens design based on a polymer lens including a control unit 80 (voice coil motor), the polymer lens 82 and an additional negative lens 84. The negative lens 84 compensates for the overall positive polymer lens focal length, such that the light 11 will still be still almost collimated after passing through the two lenses. The additional negative lens 84 is used to allow the beam to be adjustable in a suitable range between convergent and slightly divergent. The polymer lens comprises a housing which holds the voice coil motor and associated mechanics, and a number of windows to protect the sensitive convex polymer surface from external influences.

The purpose of the adjustment is to compensate for aberrations induced by the complete optical system. The focusing system actually comprises a number of lenses and the skin itself. This system may vary due to a number of causes:
(i) The user or operator selecting a different set of focusing lenses to change the treatment depth inside the skin.
(ii) The incident laser beam undergoing changes due to e.g. changes in operating temperature.
(iii) Change of the refractive index profile in the skin being treated owing to different hydration levels etc.

The adjustment may slightly vary the divergence of the beam incident on the objective lenses (while keeping the diameter of the beam mostly unaffected), which can be used to reduce the influence of the effects mentioned above on the focusing quality. Furthermore, optical simulation has shown that by using these kinds of tools also higher order aberrations can be effectively reduced (in particular 3rd order spherical aberrations).

The adjustment controls the focal depth by compensating for aberration by introducing additional convergence or divergence.

The variable lens design is placed before the aspheric lens 72 of the focusing system 23.

In order to limit the impact of the variable divergence on the diameter of the beam incident on the aspheric lens 72 of the focusing system 23, the aberration correction elements are placed as close as possible to the input to the scanning system 21, effectively limiting the amount of space that is available for placement of mechanical components and scanning motors. The correction system may thus be part of the handpiece of the device.

Figure 9:
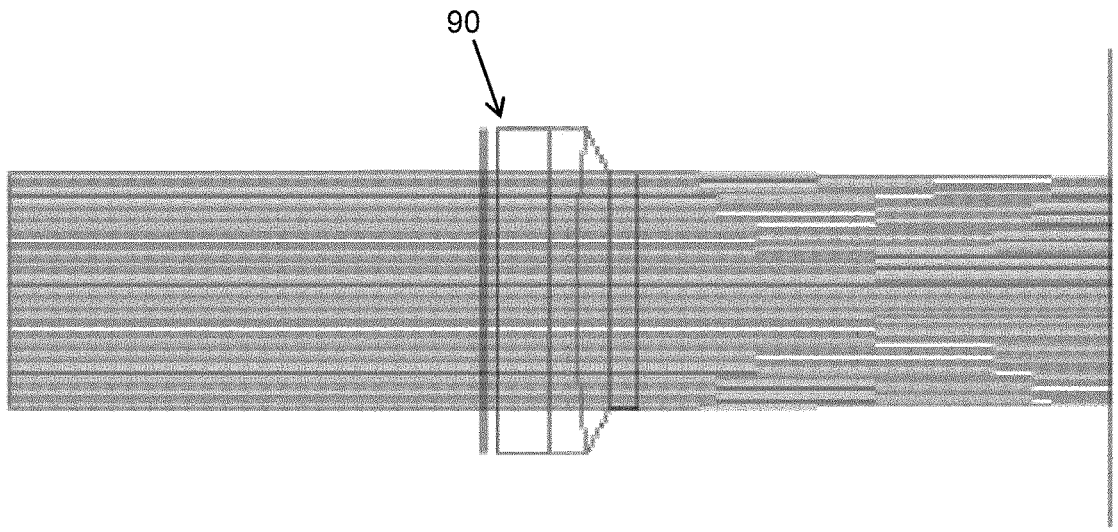
FIG. 9 shows the ray paths through a system of beam compression, aberration compensation, scanning, beam expansion and focusing.

FIG. 9 shows a ray trace of the electrowetting lens 90 used for aberration correction. The lens introduces a very small amount of convergence. No additional compensation for initial curvature is required for this lens. The lens may instead be required to introduce a small amount of divergence. The incident beam is close to collimated and the required correction is typically small.

Figure 10:
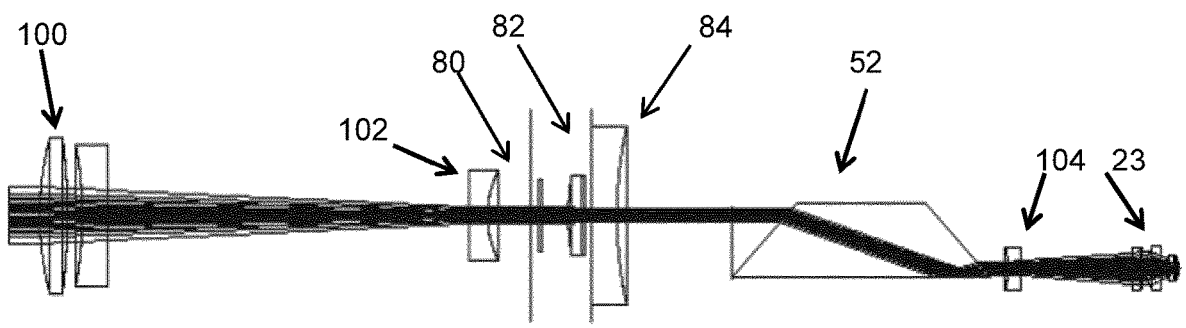
FIG. 10 shows the system of FIG. 1 modified to include the lens system for aberration compensation.

FIG. 10 shows a ray trace of the complete assembly of all optical elements. These include a 3× beam compression 100 unit and a negative lens 102 which together reduce the beam size so that a smaller prism may be used but also reverse the beam expansion used in the articulating arm which connects the handpiece to the laser source if any. The input beam for example has a diameter of 6 mm. The aberration correction unit (including the parts 80, 82, 84 of FIG. 8) is shown, the dove prism 52 (could be other type of optical device in the scanner), the beam expander 104 and the adjustable focusing system 23.

Figure 11:
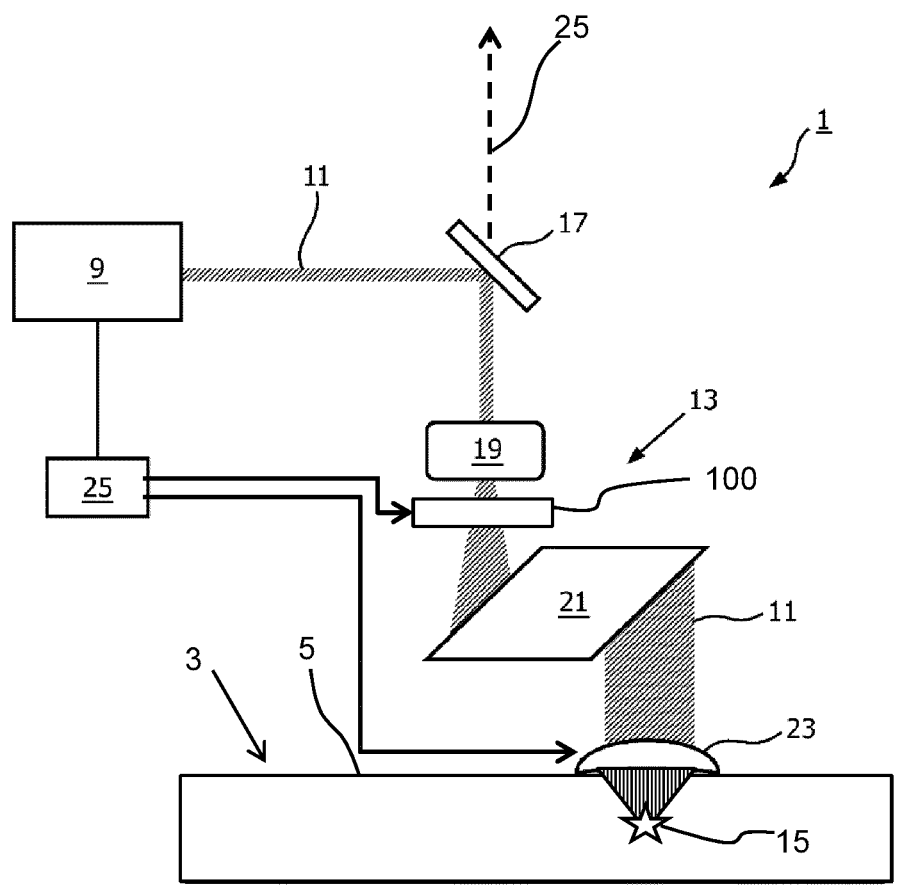
FIG. 11 shows a device according to an embodiment of the invention.

FIG. 11 shows the system of the invention modified to include the adjustable lens system 100 for aberration correction of the focusing system 23. The adjustable lens system 100 is controlled by the controller 25 in synchronism with the adjustment of the focus depth setting of the focusing system 23, so that aberration correction is matched to the setting of the focusing system 23. The adjustable lens system 100 is provided at the input to the scanning system 21. Hence it does not need to rotate with the scanning system.

Thus, the aberration correction system, which may be bulky and heavy does not need to be scanned with the focusing system 23 (objective lenses), which would make scanning at high speeds and in continuous motion difficult because of the need of gliding electrical contacts etc. and because the motion could also induce vibration to the tunable lenses themselves. The focusing lenses and mounts forming the focusing system 23 weigh only a few grams. The polymer tunable lens for example weighs only tens of grams excluding the associated mounts and plano-concave lenses.

The system of FIGS. 1 and 10 have one particular set of optical components between the laser and the focusing system. However, this arrangement is not intended to be limiting. The feedback system of the invention may be used in different system configurations with a smaller or greater number of components.

The aberration correction is of particular interest for an electrically adjustable focusing system such as described above. However, the aberration correction may also be used in connection with a mechanically adjustable focusing system such as shown in FIG. 2.

In particular, not all aberrations can be controlled in a selectable set of adjustments, so fine tuning may be desired on a case by case basis or in a dynamic manner.

The aberration correction system alone does not have sufficient power to affect the focusing depth significantly.

With the device according to the invention, the focusing system and preferably also the scanning system and/or the beam manipulation system 19 and beam reflecting system 17 may be part of a handheld device or piece that can be held by a user during treatment of a subject.

In such case there may be an articulating arm between the laser source 9 and the beam reflecting system 17 to guide the source light to the handpiece. Other ways of providing the light from the source to the handpiece or the scanning system may be used as well.

The light source 9 can be controllable with an optional controller 25, which may provide a user interface for setting parameters of the device and/or providing feedback to the user during a treatment. The user interface can be of hardware or software with buttons and knobs. Also, one or more parts of the optical system 13 may be controllable with an optional controller (not shown), which may be integrated with a light source controller 25 to control one or more properties of the target position and/or the focal spot.

The beam reflecting system 17 can comprises a dichroic beam splitter which reflects the laser light but passes visible wavelength light. Thus, reflected visible wavelength light from the skin 3, possibly generated by a LIOB event, is captured by the optical system and is provided as a feedback signal 25 which can be used for controlling the system either manually or automatically. Such feedback system is not necessary to implement the invention, but is advantageous for focus depth control etc. if needed. The focusing depth provided by the focusing system 23 is preferably adjustable. Thus can be based on feedback provided by feedback signal 25. Other types of feedback based on light can be used as well in this way.

The feedback can be used for observing what area was and is treated at a certain point in time. A surface area tracker can be used to map what areas have been treated.

The skin treatment may comprise a hair removal shaving process. During use, the focusing system 23 is moved over the skin surface to be shaved. The focusing system forms an exit window for allowing the incident light beam to leave the device. The focusing system then forms an optical blade.

The skin treatment may comprise skin rejuvenation device for reducing wrinkles that may appear in human skin as a result of normal aging processes. During use, the focusing element is pressed onto or kept close to the skin to be treated. The exit window formed by the focusing system (part of the exit lens as in this example) is held parallel to the skin and the incident light beam leaves the exit window and enters the skin in a direction substantially perpendicular to the skin surface.

The outermost layer of the epidermis is the stratum corneum which, due to its microscopic fluctuations in roughness, impedes the coupling of light between the device 1 and the skin 3. For this reason, a coupling fluid is preferably provided between the focusing system (the output lens or window) and the skin, with a refractive index which aims to match that of the skin and/or an exit lens of the focusing system. An immersion fluid may be provided between the focusing system and the (skin) surface. Preferably, an immersion fluid is used with a refractive index close to the refractive index of the skin contact lens of the focusing system 23 and the skin or hair where the LIOB is to occur. For this purpose, fluids with a refractive index of about 1.4 to about 1.5 are suitable. Also water, although having a somewhat lower refractive index of 1.33, may for some devices and applications be a suitable immersion fluid.

An alternative way of coupling the laser light from the device (e.g. the exit window such as the lens) into the skin is described in WO2013/128380. In that case an optical foil (reference 14 in FIG. 1 of WO2013/128380) transparent for the laser light is used with a coupling fluid (reference 13 in FIG. 1 of WO2013/128380) between lens or exit window and transparent foil and a coupling fluid (15, reference to FIG. 1 of WO2013/128380) between skin and optical foil. The fluid 13 may still allow rotation of the exit lens over the coupling foil while the foil is more or less fixed to the skin. For details towards the coupling fluids and optical foil the reader is referred to WO2013/128380, which content is incorporated by reference. At least details relating to the coupling fluids and transparent optical foil are part of the current description, without repeating them here for sake of brevity.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A light based skin treatment device configured to generate laser induced optical breakdown in a mammal tissue, the device comprising:
   a light source configured to provide a pulsed light beam;
   a beam scanner configured to receive the pulsed light beam and output a scanning pulsed light beam; and
   a focusing system configured to focus the scanning pulsed light beam into a focal spot for positioning in the mammal tissue to cause the laser induced optical breakdown,
   wherein during scanning by the beam scanner, at least one part of the beam scanner is rotated through at least one 360 degree rotation to change a path of the scanning pulsed light beam;
   wherein changing the path of the scanning pulsed light beam correspondingly changes the positioning of the focal spot in the mammal tissue;
   wherein during the at least one 360 degree rotation, the path of the scanning pulsed light beam is a continuously curved path;
   wherein the beam scanner comprises a beam changer configured to receive the pulsed light beam having a first beam axis and output the scanning pulsed light beam having a second beam axis that is substantially parallel to the first beam axis, and laterally shifted with respect to the first beam axis.

2. The light based skin treatment device according to claim 1, wherein the focusing system is configured to move with the scanning pulsed light beam along the path during the scanning by the beam scanner.

3. The light based skin treatment device according to claim 1, wherein the beam scanner comprises:
 a rotator mechanism including a beam changing part configured to rotate the at least one part of the beam scanner about the first axis.

4. The light based skin treatment device according to claim 3, wherein the focusing system is coupled to the beam changing part in order to rotate the focusing system.

5. The light based skin treatment device according to claim 3, wherein the beam changing part comprises at least two reflectors that output the scanning pulsed light beam having the second beam axis from the pulsed light beam having the first beam axis.

6. The light based skin treatment device according to claim 3, wherein the beam changing part comprises at least one prism that changes the light path to the deflected light path.

7. The light based skin treatment device according to claim 6, wherein the at least one prism comprises a rhomboid prism or a dove prism.

8. The light based skin treatment device according to claim 3, wherein the first beam axis and the second beam axis define a distance measured perpendicularly to the first beam axis, and further comprising a further mechanism that changes the distance.

9. The light based skin treatment device according to claim 8, wherein the further mechanism comprises:
 at least one beam refractive or reflective surface which can be tilted with regard to the first beam axis, or
 at least two beam refractive or reflective surfaces between which a distance can be changed.

10. The light based skin treatment device according to claim 1, wherein the focusing system comprises:
 a pre-focusing lens that increases a convergence of the scanning pulsed light beam; and
 a focusing lens having convex light input and light exit surfaces.

11. The light based skin treatment device according to claim 10, further comprising a focus controller that controls a distance from the focusing system to the focal spot by adjusting a spacing between the pre-focusing lens and the focusing lens.

12. The light based skin treatment according to claim 1, comprising:
 a beam compressor part arranged before the beam scanner; and
 a beam expander after the beam scanner.

13. The light based skin treatment according to claim 1, further comprising an adjustable lens system arranged in a light path before the beam scanner that provides compensation for aberration in the focusing system.

14. The light based skin treatment device according to claim 1, wherein an axis of the scanning pulsed light beam is substantially parallel to an axis of the pulsed light beam.

15. The light based skin treatment device according to claim 1, wherein the positioning of the focal spot in the mammal tissue follows the continuously curved path during the at least one 360 degree rotation.

16. The light based skin treatment device according to claim 1, wherein the positioning of the focal spot in the mammal tissue is situated at a non-zero radial distance orthogonal to an axis of the pulsed light beam.

17. The light based skin treatment device according to claim 16, wherein the radial distance varies during scanning.

18. The light based skin treatment device according to claim 16, wherein the radial distance is fixed during scanning.

* * * * *